(12) United States Patent
Viswanathan

(10) Patent No.: US 6,927,310 B2
(45) Date of Patent: Aug. 9, 2005

(54) TRIPROPYLENE GLYCOL PRODUCTION

(75) Inventor: Krishnan Viswanathan, Houston, TX (US)

(73) Assignee: Equistar Chemicals, LP, Houston, TX (US)

(*) Notice: Subject to any disclaimer, the term of this patent is extended or adjusted under 35 U.S.C. 154(b) by 0 days.

(21) Appl. No.: 10/686,456

(22) Filed: Oct. 15, 2003

(65) Prior Publication Data

US 2005/0085673 A1 Apr. 21, 2005

(51) Int. Cl.[7] ............................................. C07C 41/42
(52) U.S. Cl. ...................... 568/699; 568/679; 568/680
(58) Field of Search ................................ 568/679, 680, 568/699

(56) References Cited

U.S. PATENT DOCUMENTS 2,683,721 A * 7/1954 Schlesinger et al. ........ 549/307
3,213,113 A * 10/1965 Randall et al. ............. 549/542
3,989,740 A * 11/1976 Broussard et al. .......... 560/224
5,672,768 A * 9/1997 Gupta et al. ................ 568/621

* cited by examiner

Primary Examiner—Rosalynd Keys
(74) Attorney, Agent, or Firm—Roderick W. MacDonald

(57) ABSTRACT

A method for forming multiple tripropylene glycol products of acrylate grade comprising forming a composition of dipropylene glycol, tripropylene glycol, tetrapropylene glycol and heavier, and at least one aldehyde, separating from said composition tripropylene glycol containing aldehyde, mixing with the thus separated tripropylene that contains aldehyde an aldehyde controlling additive to form a first individual tripropylene glycol product that contains glycol controlling additive and has an aldehyde content below that required for acrylate grade tripropylene glycol, separating from the remainder of the composition a tripropylene glycol concentrate, adding an aldehyde controlling additive to the concentrate, and separating from the concentrate a second individual tripropylene product that has an aldehyde content below that required for acrylate grade tripropylene glycol and is free of aldehyde controlling additive.

5 Claims, 3 Drawing Sheets

FIG. 2 Invention

_US 6,927,310 B2_

TRIPROPYLENE GLYCOL PRODUCTION

BACKGROUND OF THE INVENTION

1. Field of the Invention

This invention relates to the production of tripropylene glycol (TPG) and, more particularly, to the production of acrylate grade TPG.

2. Description of the Prior Art

Acrylates, including methacrylates, are valuable chemical building blocks that find many commercial applications such as surface coatings, adhesives, leather and textile finishing, paper coating, and the like. Many commercial acrylate uses require good clarity (transparency) of the final article, e.g., transparent containers.

Urethanes also have valuable chemical uses in the formation of flexible foams, rigid foams, and laminates. Polyurethanes have a wide range of commercial uses such as soft cushioning applications in furniture, vehicles, and the like; laminate padding in clothing; rigid foam insulation; and finishes/varnishes, particularly for surfaces that undergo abusive and/or abrasive wear.

Producers of acrylates and urethanes that go into the making of polyacrylates and polyurethanes often use TPG in their manufacturing processes.

TPG is typically made by hydrolyzing propylene oxide in known manner, but, in so doing, monopropylene glycol (MPG), dipropylene glycol (DPG), tetra propylene glycol (TTPG) and heavier glycols; and one or more aldehydes, including propionaldehyde and aldehydes derived from DPG, TTPG, and the like, are formed in admixture with the desired TPG. Essentially pure TPG must be extracted from this mixture before it can be used in the commercial manufacture of acrylates and urethanes.

Aldehydes mentioned here in above tend to be carried along with the TPG into the acrylate and urethane manufacturing processes. Such aldehydes can have an adverse affect on the clarity of acrylate products that is not tolerable in certain commercial applications. Urethane manufacturing requirements as to the aldehyde content of the TPG used in such manufacture is not as rigid as acrylate manufacturing requirements since, for example, polyurethane product clarity is not important in most polyurethane uses. Therefore, TPG used in urethane manufacturing can have a larger aldehyde content than TPG used in acrylate manufacturing.

Accordingly, there is what is known in the art as acrylate grade TPG and urethane grade TPG. At present, the dividing line between the two grades of TPG is 20 parts per million (ppm) of total aldehyde content in the TPG in question. Acrylate grade TPG can contain no more than 20 ppm of total aldehyde content. Urethane grade TPG can contain more than 20 ppm of total aldehyde content. Both ppm contents are reported as ppm "CHO."

Therefore, it is important to control the aldehyde content of the final TPG product when the TPG is produced for use in the manufacture of acrylates and urethanes, and particularly acrylates.

The aldehyde content of a TPG product is typically controlled by the use of at least one additive (agent) which reacts with and neutralizes most, if not all, of the aldehyde present in that product. Such aldehyde controlling (reducing) additives are well known in the art and include alkali borohydrides, particularly sodium borohydride. The borohydride, at present, reduces the aldehyde content of TPG to the lowest levels achievable. By use of such additives, the aldehyde content is substantially reduced, if not eliminated, but the additive itself can be left in the TPG product.

Depending on its individual processes and desires, an acrylate manufacturer may be willing to use a TPG product that contains such aldehyde controlling additives, or may, on the other hand, require that the TPG product it buys be essentially free of such additives. In either case, to be acrylate grade, the TPG product must contain no significant amount, no more than 20 ppm, total aldehyde, and often no more than 10 ppm aldehyde.

Accordingly, it is desirable to be able to provide an acrylate grade TPG product either with or without the presence of an aldehyde controlling additive or additives. This invention does just that, and does so with significant cost savings over the practice of the prior art.

The prior art practice, which will be discussed in greater detail here-in-after, has been to make in a single TPG product that is essentially free of aldehyde controlling additive. This has necessitated the transport of large volumes of TPG to a final processor (toiler) which, for a fee, separates out an essentially pure, single, final TPG product that contains essentially no significant amount, as defined above, of such additive.

SUMMARY OF THE INVENTION

In accordance with this invention, two separate final TPG products can be produced. The first such product is acrylate grade and contains aldehyde controlling additive, but it has the lowest aldehyde content of the two products. The second such product also is acrylate grade, but it has a larger aldehyde content than the first product, and is essentially free of aldehyde controlling additive.

Thus, this invention has a distinct processing advantage in flexibility. It can provide a TPG product that can meet the requirements of acrylate manufacturers that demand the lowest possible aldehyde content (the first product above), and at the same time provide a concentrate that is a source of raw material for a TPG product that is also acrylate grade but which is essentially free of aldehyde controlling additive (the second product above). This raw material can then readily be made into the second product aforesaid in the same (single) process or a subsequent independent process as shown in FIG. 3 hereof.

In addition to its processing flexibility advantages, this invention has multiple manufacturing cost advantages. As explained in detail here-in-after, by producing the aforementioned concentrate of this invention, the transportation of a very substantial volume of TPG containing material to a toiler for separation of an additive-free TPG product is materially reduced. By virtue of such concentrate, this invention reduces not only the cost of transporting a very large volume of material to the toiler, but also the toller's charge for making the final separation from the concentrate of a TPG product free of aldehyde controlling additive. Finally, the bottoms material remaining after the second product of this invention is recovered is of a substantially smaller volume than that of the prior art.

DETAILED DESCRIPTION OF THE INVENTION

Figure 1:
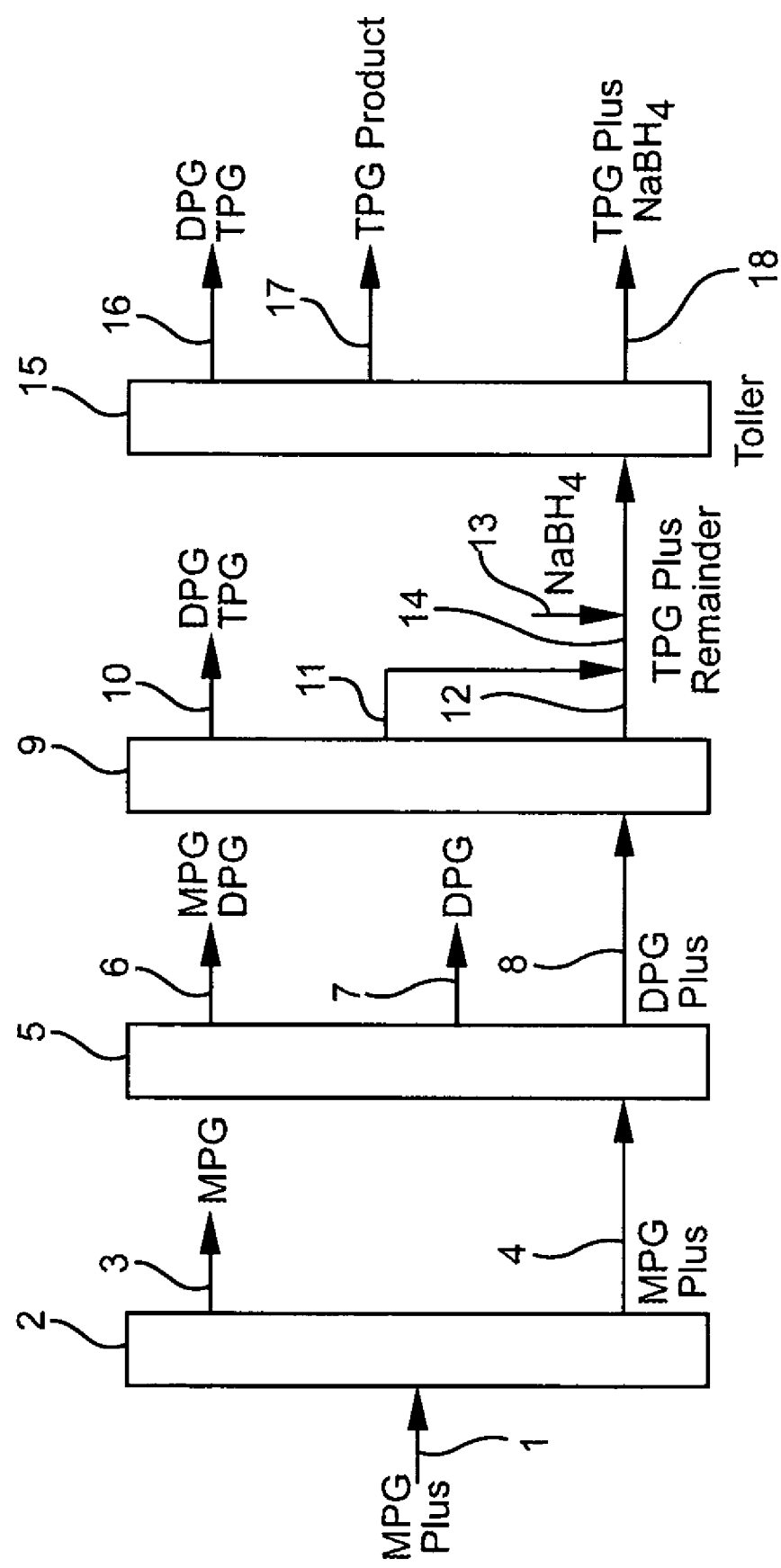
FIG. 1 shows a block-flow diagram of the prior art process mentioned above.

FIG. 1 shows an exemplary and typical prior art process used commercially at present wherein the mixture of glycol and aldehyde formed from reacting propylene oxide with water, as discussed above, is used as feed 1 to a conventional distillation tower (column) 2 for the removal of an overhead MPG stream 3 from feed 1. The remainder of the MPG depleted feed comprises MPG and heavier glycol molecules plus one or more aldehydes (MPG plus), and it is passed by way of conduit or line 4 to a separate distillation tower 5. In tower 5, a mixture of MPG and DPG is removed overhead at line 6, and an intermediate DPG stream is removed medially at 7. The remainder of stream 4 comprises DPG and heavier glycol molecules plus at least one aldehyde (DPG plus), and it is passed via line 8 to a separate distillation tower 9 wherein an overhead stream 10 composed essentially of the remaining DPG and a minor amount of TPG is removed. The remainder of stream 8 is substantially depleted in MPG and DPG and, as represented by the combination of side stream 11 and bottom stream 12, is stream 14. Stream 14 comprises TPG and heavier glycol molecules plus at least one aldehyde (TPG plus remainder). This TPG plus remainder stream 14 is now ready for processing to produce the desired prior art TPG product.

The prior art practice has been to ship this TPG plus remainder stream 14 which contains most of the TPG present in the original feed to an independent toiler for the extraction of the desired TPG product. For sake of simplicity, the transport by truck, train, ship, or a combination thereof, to a toiler is represented by line 14, although, in reality, such transportation is not as straight forward nor inexpensive as is represented by line 14.

For example, in a typical TPG plant, stream 14 can vary from 14 to 18 million pounds per year (mpy). At a typical 2 cent per pound transportation cost, the transportation fees are substantial for this size of volume. Add to these transportation costs the toller's fee of from 10 to 25 cents per pound, and substantial total costs are realized in forming from stream 14 a single product 17, which product is essentially free of aldehyde controlling agent. As shown later, this invention reduces both the transportation and toiler costs. In the toller's plant, stream 18 can be as large as 2 mpy which is a substantial non-product stream to be disposed of in some form or fashion.

At the toller's plant, stream 14 is mixed via line 13 with at least one aldehyde controlling additive such as sodium borohydride (NaBH4). The amount of additive used can vary widely, but it is that which is sufficient to reduce the aldehyde content of stream 14 to a level that would be acrylate grade as aforesaid, a straight forward determination for one skilled in the art. Generally, from about 50 to about 2,000 parts per million (ppm) weight percent additive(s) are used based on the total weight of the mixture. The mixture resulting from streams 14 and 13 is passed into a conventional distillation tower 15. An overhead fraction 16 is removed from tower 15 which is composed essentially of remaining DPG and a minor amount of TPG. The sole prior art TPG product is separately removed as an intermediate stream 17. This product is essentially free of additive. The tower bottoms 18 contain TPG and heavier glycol molecules (TPG plus) and the additive remaining from line 13.

Thus, this prior art process produces a single acrylate grade TPG product 17 that contains essentially no aldehyde controlling additive. Because product 17 contains no additive, this product does not have the lowest possible aldehyde content, and may not be acceptable to acrylate manufacturers who demand the lowest possible aldehyde content in the TPG they purchase for their manufacturing purposes.

Figure 2:
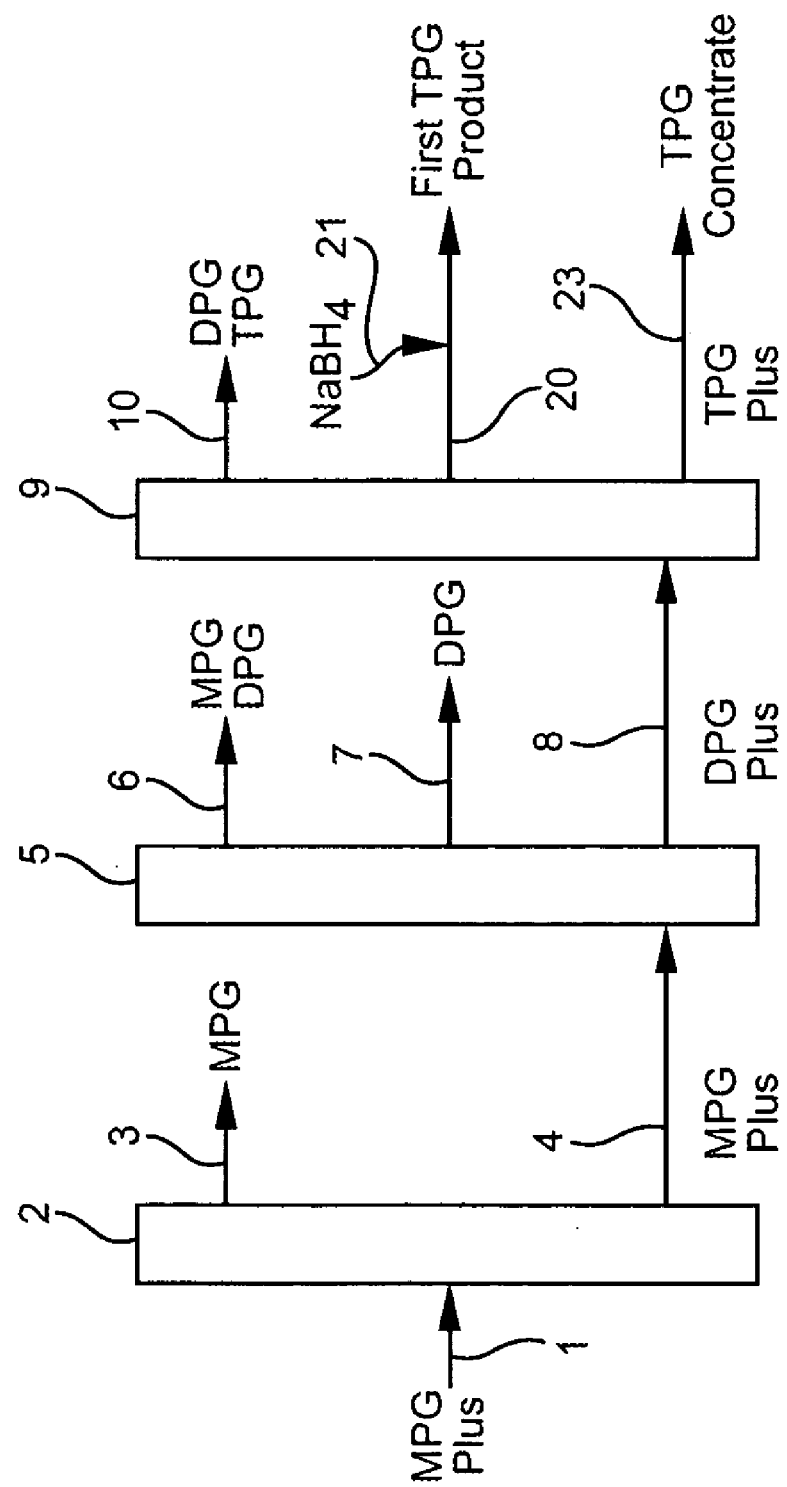
FIG. 2 shows a block-flow diagram of a process within this invention.

For sake of ease of comparison only, FIG. 2 shows the same towers 2, 5, and 9 as FIG. 1, and the same streams 3 through 10 of FIG. 1. This invention may use such a processing arrangement or a different arrangement known in the art and is not limited to this particular arrangement. Where this invention departs from the sample prior art process of FIG. 1 is in tower 9.

In tower 9 feed 8 comprises a mixture of DPG, TPG, TTPG, glycols heavier than TTPG, and at least one aldehyde compound. A blend of mostly DPG and a minor amount of TPG is removed via stream 10 in normal fashion. After this removal, the material remaining in tower 9 contains a major amount, at least about 85 weight percent (wt %), TPG. The material also contains minor amounts of DPG and lighter molecules (less than 1 wt %), TPG and heavier glycol molecules (less than about 13 wt %), and one or more aldehydes (less than 1 wt %). All wt % are based on the total weight of such material. The prior art, as shown in FIG. 1, stream 14, transports in one form or fashion the entirety of this material to a toller for separate processing as described above.

This invention departs from the prior art in that it operates tower 9 in such a manner, known in the art, to effect a separate intermediate cut from this material, that cut being stream 20 of FIG. 2. In accordance with this invention, stream 20, in essentially its entirety, is deliberately kept physically separate and is mixed with at least one aldehyde controlling additive 21. This produces the first final TPG product of this invention. This product is acrylate grade. It contains additive 21 and therefore has the lowest aldehyde content possible, if not essentially zero.

By separately removing product 20, the material left in tower 9 is a concentrate that contains residual TPG and aldehyde and is removed as bottoms 23. As discussed above, prior art stream 14 is typically a volume of 14 to 18 mpy. Concentrate stream 23 is typically a volume of 4 to 6 mpy. The elimination of transporting and toller treating costs for 10 to 12 mpy is clearly a substantial cost saving.

Stream 23 is a concentrated source of raw material for the second, final TPG product of this invention. Stream 23 can be processed as part of a single process to form such second TPG product, or can be processed in the manner of FIG. 1, i.e., transported to an independent toiler for processing. Again for ease of comparison, the formation of the second product of this invention will be discussed in the manner of FIG. 1, although the second product of this invention need not necessarily be formed in this manner, other ways being obvious to those skilled in the art.

Figure 3:
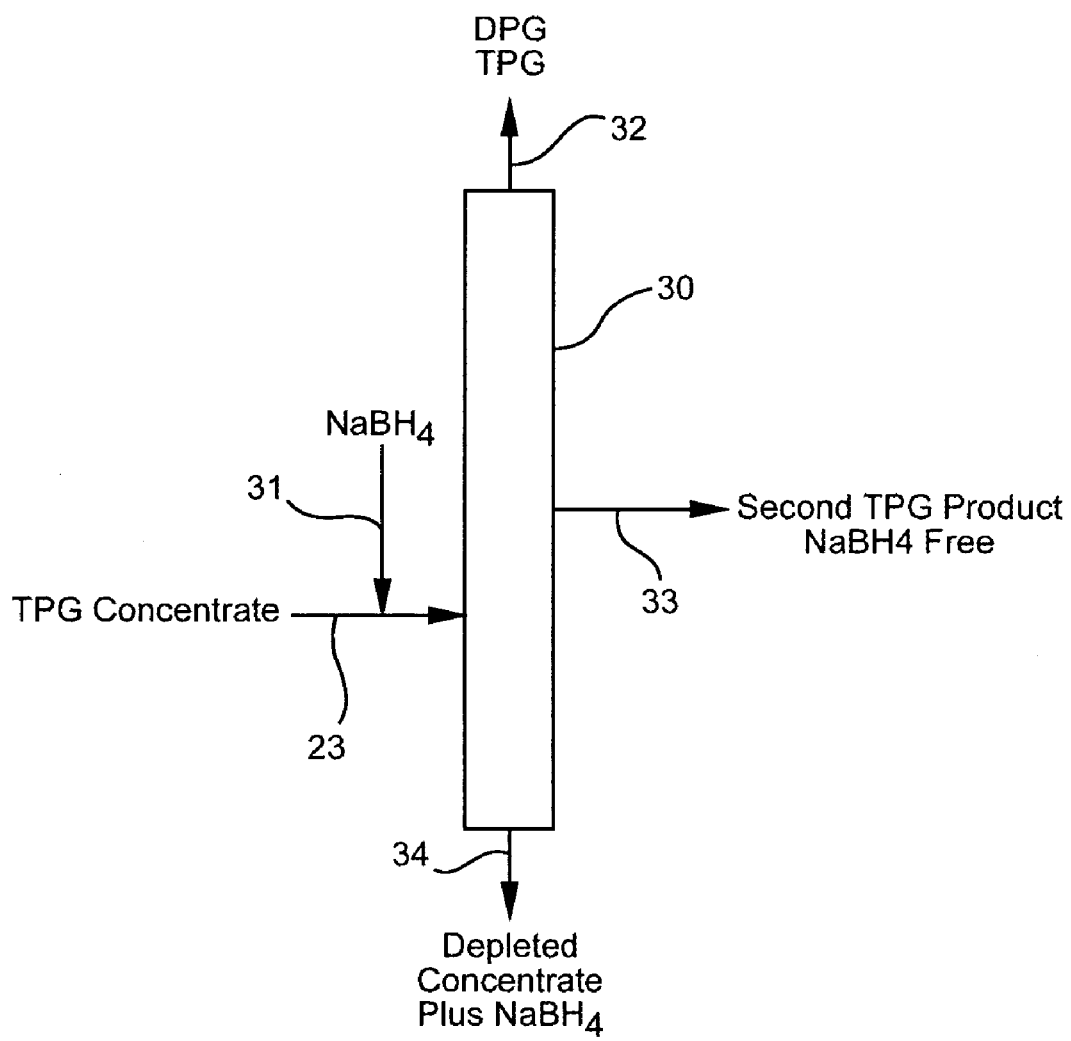
FIG. 3 shows a block-flow diagram of one independent process for producing the second TPG product aforesaid.

FIG. 3 shows concentrate 23 being subjected to distillation in tower 30, which tower can be a toller's column or another tower in the TPG manufacturer's plant. Concentrate 23 is mixed with aldehyde controlling additive 31 and then fed to tower 3 wherein it is fractionated in known manner to form an overhead 32 comprising essentially DPG and TPG and an intermediate cut 33 which is the second final TPG product of this invention. Tower 30 operating conditions are controlled in known manner so that second product 33, unlike first product 20, is essentially free, if not totally free, of aldehyde controlling additive. The bottoms 34 of tower 30 are concentrate 23 depleted of TPG and containing the remaining additive from line 31.

Bottoms 34 are of a volume substantially less than the 2 mpy of line 18. Thus, by the practice of this invention, substantially less bottoms product must be disposed of or otherwise handled.

Accordingly, by the use of this invention, two separate and distinct acrylate grade TPG products are formed, the first product with additive and the lowest aldehyde content of the two products, and the second product with no additive; along with the elimination of the transportation to and toiler treating of a large volume, e.g., 10 to 12 mpy, of material, and a smaller bottoms volume of which to dispose.

Any known aldehyde controlling additive can be used in this invention. The most effective additives for reacting with and neutralizing aldehydes are alkali metal borohydrides, particularly sodium borohydride. Other known additives such as methyl ether hydroquinone can be employed in this invention. All are employed by simple mixing at normal processing temperature and pressure, well known in the art, in an amount effective to reduce the aldehyde content of the stream they are mixed with to a level equal to or less than 20 ppm.

EXAMPLE

A mixture of DPG, TPG, TTPG, glycols heavier than TTPG, and at least one aldehyde is subjected to distillation conditions in tower 9 of FIG. 2. Tower 9 is operated at less than 50 millimeters absolute pressure, and a bottom temperature of about 430° F. to produce an overhead 10 consisting essentially of a major amount of DPG and a minor amount of TPG. The material remaining in tower 9 after removal of the overhead consists essentially of about 96.1 wt % TPG, less than 0.1 wt % DPG, about 3.8 wt % TTPG and heavier glycols, and about 300 ppm aldehyde.

Under the distillation conditions aforesaid, physically separate and independent intermediate stream 20 is removed and consists essentially of TPG and 270 ppm aldehyde.

Sodium borohydride stream 21 is mixed with stream 20 under ambient conditions of temperature and pressure in an amount of less than 50 ppm wt %, which is sufficient to reduce the aldehyde content of that stream to less than 20 ppm and form the first product of the invention.

Concentrate 23 is removed from tower 9. Concentrate 23 consists essentially of about 70.0 wt % TPG, less than 0.1 wt % DPG and lighter, about 30.0 wt % TTPG and heavier, and about 270 ppm aldehyde. Concentrate 23 is fractionated in tower 30 of FIG. 3. Tower 30 is operated at a pressure of about 15 millimeters absolute pressure, a bottom temperature of about 400° F., and an overhead temperature of about 330° F. Intermediate stream 33 is removed from tower 30, and contains about 50.0 wt % TPG, the remainder being DPG and TTPG. The bottoms 34 contain essentially TTPG and heavier plus sodium borohydride and less than 1 wt % TPG.

As can be seen from the example, two acrylate grade TPG products are formed, one with sodium borohydride additive, and one without.

What is claimed is:

1. In a method for recovering multiple separate tripropylene glycol products from a mixture of dipropylene glycol, tripropylene glycol, tetrapropylene glycol, glycols heavier than tetrapropylene glycol, and at least one aldehyde compound, wherein a blend of dipropylene glycol and tripropylene glycol is removed from said mixture thereby leaving a composition that contains a major amount of tripropylene glycol and minor amounts of dipropylene glycol, at least one aldehyde, tetrapropylene glycol, and glycols heavier than tetrapropylene glycol, the improvement comprising separating from said composition a first stream consisting essentially of tripropylene glycol and aldehyde thereby leaving the remainder of said composition as a second stream concentrate that contains residual tripropylene glycol and aldehyde, deliberately keeping said first stream physically separate from said second stream concentrate, mixing with said first stream at least one additive that reacts with and neutralizes said aldehyde, said additive being employed in an amount sufficient to produce a first individual tripropylene glycol product that contains no more than 20 ppm of said aldehyde and which contains said neutralizing additive, and separately removing said second stream concentrate to a separate processing step to form a second separate individual tripropylene glycol product that contains essentially no neutralizing additive.

2. The method of claim 1 wherein said second stream concentrate is mixed with at least one additive that reacts with and neutralizes said aldehyde, thereafter separating from said second stream concentrate that contains said additive a second separate individual tripropylene glycol product that contains no more than 20 ppm of aldehyde and which contains essentially no additive, and separately recovering from said second stream concentrate a third stream which contains said additive, tripropylene glycol, tetrapropylene glycol, and glycols heavier than tetrapropylene glycol, whereby two separate acrylate grade tripropylene glycol products are produced, one product containing neutralizing additive and one product essentially free of neutralizing additive.

3. The method of claim 1 wherein said neutralizing additive is at least one alkali metal borohydride.

4. The method of claim 1 wherein said composition of claim 1 contains at least about 85 weight percent tripropylene glycol, no more than about 1 weight percent dipropylene glycol and lighter molecules, no more than about 13 weight percent tetrapropylene glycol and heavier glycols, and no more than about 1 weight percent aldehyde, all weight percents being based on the total weight of said material.

5. The method of claim 1 wherein said first tripropylene glycol product contains an amount of neutralizing additive sufficient to reduce the aldehyde content of said first product to substantially below 20 ppm.

* * * * *